United States Patent [19]

Ikeda et al.

[11] Patent Number: 5,183,660
[45] Date of Patent: Feb. 2, 1993

[54] POLYETHYLENE GLYCOL DERIVATIVES, THEIR MODIFIED PEPTIDES, METHODS FOR PRODUCING THEM AND USE OF THE MODIFIED PEPTIDES

[75] Inventors: Yoshiharu Ikeda, Somerville, Mass.; Yoshiyuki Kai, Kobe; Keiichi Ono, Sakai, both of Japan

[73] Assignee: Sumitomo Pharmaceuticals Company, Limited, Osaka, Japan

[21] Appl. No.: 745,496

[22] Filed: Aug. 15, 1991

[30] Foreign Application Priority Data

Aug. 28, 1990 [JP] Japan ................... 2-227541

[51] Int. Cl.$^5$ ................... A61K 37/02; A61K 37/48; C07C 63/04; C07C 65/21
[52] U.S. Cl. ................... 424/94.3; 435/188; 514/2; 514/12; 530/345; 530/399; 530/406; 530/410; 562/465; 562/473
[58] Field of Search ............... 530/345, 389, 406, 410, 530/307, 399, 391.1; 568/629, 630, 648; 562/465, 473, 493, 496; 528/425; 514/2, 12; 424/94.4, 94.64, 94.3; 435/177, 188

[56] References Cited

U.S. PATENT DOCUMENTS

| 4,179,337 | 12/1979 | Davis et al. ................... 435/181 |
| 4,268,442 | 5/1981 | Kondo et al. ................... 562/465 |
| 4,590,291 | 5/1986 | Boshagen et al. ................... 562/473 |
| 4,791,192 | 12/1988 | Nakagawa et al. ................... 530/410 |

FOREIGN PATENT DOCUMENTS

| 0154316 | 9/1985 | European Pat. Off. . |
| 0210761 | 2/1987 | European Pat. Off. . |
| 0271289 | 6/1988 | European Pat. Off. . |
| 331085 | 9/1989 | European Pat. Off. ............. 562/473 |
| 0335423 | 10/1989 | European Pat. Off. . |
| 0340741 | 11/1989 | European Pat. Off. . |
| 0400486 | 12/1990 | European Pat. Off. . |
| 61-42558 | 9/1986 | Japan . |
| WO-A-8906546 | 7/1989 | PCT Int'l Appl. . |
| 1174535 | 12/1969 | United Kingdom ................. 562/465 |

OTHER PUBLICATIONS

Tetrahedron, vol. 46, No. 20, Sep. 29, 1990, pp. 7289-7300.
Tetrahedron Letters, vol. 31, No. 20, Jun. 12, 1990, pp. 2929-2932.
Protein Hybrid, 3, 277-287, Kyoritsu Shuppan (Apr. 20, 1980).
Abuchowski et al., J. Biol. Chem., vol. 252, No. 11 (1911), pp. 3578-3581.
Leonard et al., Tetrahedron, vol. 40, No. 9 (1984), pp. 1581-1584.
Abuchowski et al., Cancer Biochem. Biophys., vol. 7 (1984), pp. 175-186.
Beauchamp et al., Anal. Biochem., vol. 131 (1983), pp. 25-33.
Matsushima et al., Chemistry Letters (1980), pp. 773-776.
Seikagaku et al., Chemistry Letters (1980), pp. 1255-1267.
Yoshimoto et al., Jpn. J. Cancer Res. (Gann), vol. 77 (1986), pp. 1264-1270.
Crossland et al., J. Org. Chem., vol. 35, No. 9 (1970), pp. 3195-3196.
Sekera et al., J. Amer. Chem. Soc., vol. 55 (1933), pp. 345-349.
Cason et al., J. Org. Chem., vol. 26 (1961), pp. 3645-3649.
Hooz et al., Canadian Journal of Chemistry, vol. 46 (1968), pp. 86-87.
Ono et al., J. Biomater. Sci. Polymer Edn., vol. 2, No. 1 (1991), pp. 61-65.

Primary Examiner—Jeffrey E. Russel
Attorney, Agent, or Firm—Wenderoth, Lind & Ponack

[57] ABSTRACT

Polyethylene glycol derivatives of the formula

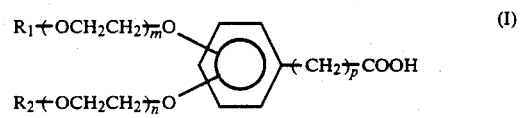

wherein $R_1$ and $R_2$ are the same or different and each represents a lower alkyl, m and n are the same or different and each represents a positive integer and p is 0 or a positive integer, peptides modified by the polyethylene glycol derivatives, methods for producing them and use of the modified peptides. The peptides modified by the polyethylene glycol derivatives (I) of the invention, as compared with the corresponding non-modified peptides, show decreased antigenicity, are considerably delayed in biological clearance, and exhibit their physiological activities effectively over a long period, rendering them very effective as pharmaceuticals as well as drugs for animals.

14 Claims, No Drawings

POLYETHYLENE GLYCOL DERIVATIVES, THEIR MODIFIED PEPTIDES, METHODS FOR PRODUCING THEM AND USE OF THE MODIFIED PEPTIDES

BACKGROUND OF THE INVENTION

This invention relates to polyethylene glycol derivatives which are novel and of use as a peptide-modifying reagent, peptides having amino groups which are modified by said polyethylene glycol derivatives, methods for production thereof and use of the modified peptides.

In recent years, with the development of research on proteins, a great number of peptides having various actions have been found. Owing to the progress of genetic recombination techniques and organic synthetic methods of peptides, it has become possible to obtain these physiologically active peptides and their structurally analogous compounds in a large amount. Many of these peptides having special activity are extremely useful as pharmaceuticals.

However, it is known that the clearance of peptides which have been administered in the circulatory system is generally very fast, and therefore improvement in durability of such peptides has been desired. Besides, since there is a risk of causing serious symptoms due to the production of antibodies in the case where the peptides are obtained from different species of animals or designed by peptide protein engineering, and they are different from those of humans in structure, improvement of the antigenicity of said peptides has been desired.

In order to use these peptides as pharmaceuticals, it is necessary to solve said problems in the aspect of their antigenicity and durability. The method of modifying the peptides chemically with macromolecular compounds is known to be extremely effective as the means by which to solve the above-mentioned problems.

Thus, polyethylene glycol derivatives have been widely used as peptide-modifying macromolecular reagents because they have excellent characteristics that they do not have immunogenicity themselves and that they do not affect the three-dimensional structures of peptides in aqueous solutions.

In modifying the amino groups at the N-terminal or in the side-chain of the lysine residues of the peptides using derivatives having one polyethylene glycol chain, there have been known a method wherein polyethylene glycol is introduced after conversion into an activated compound such as an acyl azide compound (Theodorus, Van Es. et al, Japanese Patent Publication (Kokoku) No. 23587/1981), the method with polyethylene glycol triazine derivatives [Frank F. Davis et al, J. Boil. Chem., 252, 3578-3581 (1977)], the method wherein an active ester of N-hydroxysuccinimide is used for introduction [Leonard M. et al, Tetrahedron, 40, 1581-1584 (1984), Abuchowski, A. et al, Cancer Biochem. Biophys., 7, 175 (1984)], the method wherein an activated compound introduced by carbonyldiimidazole is used [Charles, O. Beauchamp et al, Anal. Biochem., 131, 25-33 (1983)], the method with polyethylene glycol aldehyde derivatives [Fujino et al, Japanese Patent Unexamined Publication (Kokai) No. 178926/1986] and so on. In the meantime, as the method wherein derivatives having two polyethylene glycol chains are used, there have been known the method with polyethylene glycol triazine derivatives (Inada et al, Japanese Patent Publication (Kokoku) No. 42558/1986 and so on) and the method with polyethylene glycol triazine carboxylic acid derivatives (Yamazaki et al, Japanese Patent Unexamined Publication (Kokai) No. 316400/1989).

Despite the fact that derivatives having two polyethylene glycol chains are more effective in terms of reduction of antigenicity than those having one polyethylene glycol chain, [Inada et al, Japanese Patent Publication (Kokoku) No. 42558/1986, Inada et al, Chemistry Letters, 733 (1980), Inada et al., Seikagaku, 52, 1255-1267 (1980)], only triazine derivatives of Inada et al and Yamazaki et al as mentioned above are derivatives having two polyethylene glycol chains and are capable of modifying amino groups, which have been known so far.

SUMMARY OF THE INVENTION

An object of the present invention is to provide derivatives having two polyethylene glycol chains, which do not posses a triazine ring and are capable of modifying amino groups in peptides.

Another object of this invention is to provide modified peptides which can be obtained by using said polyethylene glycol derivatives.

The present inventors conducted intensive researches and studies for the purpose of attaining the above-mentioned objects to find that the below-mentioned polyethylene glycol derivatives (I) could modify amino groups in peptides. Further researches and studies resulted in completion of the present invention.

The first invention of the present application relates to polyethylene glycol derivatives (I) of the formula

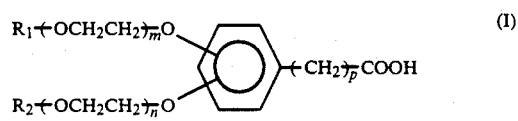 (I)

wherein $R_1$ and $R_2$ are the same or different and each represents a lower alkyl, m and n are the same or different and each represents a positive integer and p is 0 or a positive integer.

The second invention of the present application relates to modified peptides which can be obtained by reacting a carboxyl group-activated compound of the polyethylene glycol derivatives (I) with peptides having amino groups.

The third invention of the present application relates to methods for producing the polyethylene glycol derivatives (I) comprising reacting a compound of the formula (III) or (III')

 (III)

 (III')

wherein $X_1$ and $X_2$ are the same or different and each represents an alkylsulfonyloxy (e.g. a lower alkylsulfonyloxy having 1-4 carbon atoms such as methylsulfonyloxy or ethylsulfonyloxy), an aromatic sulfonyloxy (e.g. toluenesulfonyloxy) or a halogen (chlorine, bromine, iodine, etc.), and $R_1$, $R_2$, m and n are as defined above, with a compound of the formula (IV)

$$HO-\underset{HO}{\underset{|}{\bigcirc}}-(CH_2)_p COOH \qquad (IV)$$

wherein p is as defined above.

The fourth invention of the present application relates to methods for producing the modified peptides comprising reaction of a carboxyl group-activated compound of the polyethylene glycol derivatives (I) and a peptide having at least one free amino group.

The fifth invention of the present application relates to pharmaceutical compositions containing a modified peptide and a pharmaceutically acceptable carrier.

DETAILED DESCRIPTION OF THE INVENTION

In formula (I), the lower alkyl groups represented by $R_1$ and $R_2$ may be in a straight-chain or branched-chain form. Preferred are, for example, lower alkyl groups having 1 to 4 carbon atoms such as methyl, ethyl, n-propyl, isopropyl and n-butyl. As regards m and n, there is no particular limitation imposed thereon, but a positive integer of 10-400, particularly 20-150 is preferable. No limitation is imposed on p, either, but 0 or a positive integer of 1-10 is preferable.

The polyethylene glycol derivatives (I) of the present invention can be easily produced by the following methods:

That is, by reacting a monoalkoxypolyethylene glycol of the formula $$R_1(OCH_2CH_2)_m OH \qquad (II)$$

$$R_2(OCH_2CH_2)_n OH \qquad (II')$$

wherein $R_1$, $R_2$, m and n are of the same meanings as defined above, with an appropriate activating reagent, preferably in the presence of a base, there is obtained an activated compound of the formula $$R_1(OCH_2CH_2)_m X_1 \qquad (III)$$

$$R_2(OCH_2CH_2)_n X_2 \qquad (III')$$

wherein $X_1$, $X_2$, $R_1$, $R_2$, m and n are as defined above.

As the activating reagents to be used in the reaction, mention may be made of, for example, ① alkylsulfonyl chlorides (as the alkyl moiety, preferred are the same lower alkyls as the above-mentioned alkyls; there may be mentioned, for example, methylsulfonyl chloride, ethylsulfonyl chloride and the like) [Ronald K. Crossland et al, J. Org. Chem., 35, 3195 (1970)], ② aromatic sulfonyl chlorides (e.g. toluenesulfonyl chloride) [Vladimir C. Sekera et al, J. Amer. Chem. Soc., 55, 345 (1933)], ③ phosphorus pentabromide [James Cason et al, J. Org. Chem., 26, 3645 (1961)] and the like, and further, ④ the compounds of the formula $C(X)_4$ [wherein X represents a halogen (e.g. chlorine, bromine)] which are used in the presence of a compound of the formula $(R')_3P$ [wherein R' represents an alkyl group (e.g. octyl), an aryl group (e.g. phenyl) or a dialkylamino group (e.g. dimethylamino)] [J. Hooz et al, Can. J. Chem., 46, 86 (1968)], and the like.

As the bases to be used in the reaction, mention may be made of pyridine, tertiary organic bases such as trialkylamine (e.g. triethylamine) and inorganic bases such as sodium hydroxide, potassium hydroxide, sodium carbonate and sodium hydride. As the reaction solvent, there can be used any per se inert solvents such as N,N-dimethylformamide, benzene, toluene, lower dialkyl ether, carbon tetrachloride, chloroform, methylene chloride, dioxane and tetrahydrofuran. Some of the above-mentioned bases such as pyridine can be used as solvents themselves. The reaction temperature is usually in the range of from 0° C. to 150° C.

Thereafter, by reacting the activated compound (III and/or III') with a dihydroxybenzene derivative of the formula (IV)

$$HO-\underset{HO}{\underset{|}{\bigcirc}}-(CH_2)_p COOH \qquad (IV)$$

wherein p is as defined above, in an appropriate solvent such as N,N-dimethylformamide or tetrahydrofuran in the presence of an appropriate base exemplified by an inorganic base such as potassium carbonate or sodium carbonate or an organic base such as triethylamine, tri-n-butylamine or diazabicyclo-2,2,2-undecene, a polyethylene derivative (I) of the formula $$\begin{matrix} R_1(OCH_2CH_2)_m O \\ R_2(OCH_2CH_2)_n O \end{matrix} \bigcirc -(CH_2)_p COOH \qquad (I)$$

wherein $R_1$, $R_2$, m, n and p are of the same meanings as mentioned above can be obtained. The reaction temperature is normally between −20° C. and 200° C. The polyethylene glycol derivatives (I) can be also produced by reacting a dihydroxybenzene derivative of the formula (IV) with the activated compounds III or III' with the same solvent, base and reacting temperature as mentioned above to obtain mono-polyethylene glycol derivatives, followed by reaction with III or III'.

The thus-produced polyethylene glycol derivatives (I) can be separated and purified to obtain ones having an optional purity by a per se known means.

Throughout the present specification, peptides mean compounds wherein two or more amino acids are bonded to each other by peptide linkage, and at least one of the constituent amino acids has at least one free amino group.

As such peptides, any peptides derived from various animals including humans, microorganisms or plants and those produced by genetic engineering and by synthesis may be employed. Examples include cytokines such as various interferons (e.g. interferon-α, interferon-β, interferon-γ), interleukin-2 and interleukin-3, hormones such as insulin, growth hormone-releasing factor (GRF), calcitonin, calcitonin gene related peptide (CGRP), atrial natriuretic peptide (ANP), vasopressin, corticotropin-releasing factor (CRF), vasoactive intestinal peptide (VIP), secretin, α-melanocyte-stimulating hormone (α-MSH), adrenocorticotropic hormone (ACTH), cholecystokinin (CCK), glucagon, parathyroid hormone (PTH), somatostatin, endothelin, substance P, dynorphin, oxytocin and growth hormone-releasing peptide [GHRP, e.g. Endocrinology, 114, 1537 (1984)], growth factors such as growth hormone (GH), insulin-like growth factor (IGF-I, IGF-II), β-nerve growth factor (β-NGF), basic fibroblast growth factor (bFGF), transforming growth factor, erythropoietin, granulocyte colony-stimulating factor (G-CSF), granulocyte macrophage colony-stimulating factor (GM-CSF), platelet-derived growth factor (PDGF) and epidermal growth factor (EGF), enzymes such as tissue plasminogen activator (t-PA), elastase, superoxide dismutase (SOD) bilirubin oxydase, catalase, uricase and asparaginase, other proteins such as ubiquitin, islet activating protein (IAP), serum thymic factor (STF), peptide-T and trypsin inhibitor, and derivatives thereof.

The production of the modified peptides of the present invention can be carried out by reacting a carboxyl group-activated compound of the polyethylene glycol derivatives (I) with peptides having amino groups. Activation of the polyethylene glycol derivatives (I) can be conducted by a known activating method for carboxyl group such as the activating method for carboxyl group as described in *Seikagaku Jikken Koza*, Vol. 1, *Tanpakushitsu no Kagaku IV*, Tokyo Kagaku Dojin and Izumiya et al, *Pepuchido Gosei no Kiso to Jikken*, Maruzen.

The desired degree of modification of the modified peptides varies depending on the purpose of modification and properties of each peptide. Thus, it is necessary to optionally select or adjust the degree of modification per peptide by adjusting the molar ratio of the carboxyl group-activated compound of the polyethylene glycol derivatives (I) to said peptides, reaction temperature, pH, etc. Accordingly, the molar ratio of the carboxyl group-activated compound of the polyethylene glycol derivatives (I) to the amino group of the peptide should be varied according to the desired degree of modification.

The reaction temperature is such that said peptides are not inactivated, and is preferably between 0° C. and 25° C.

While a reaction pH is set for any pH above 4.5 and which does not inactivate the peptides, since the polyethylene glycol derivatives (I) of the invention can be reacted at any pH above 4.5, it is generally between 6 and 9.

As the solvent to be used in the reaction, there can be used any solvent which does not prevent the reaction. Such solvents include, for example, buffer solutions such as phosphate buffer solution, borate buffer solution, an aqueous solution of sodium carbonate, an aqueous solution of sodium hydrogen carbonate, N-ethylmorpholine-acetic acid buffer solution, sodium maleate buffer solution and sodium acetate buffer solution. There can be added an organic solvent which does not inactivate the peptides and are inert to the reaction, exemplified by lower alcohols such as methanol, ethanol and propanol, acetonitrile, dioxane, tetrahydrofuran and the like. The sufficient reaction time is from 1 to 72 hours.

After the completion of the reaction, the reaction mixture is purified by a conventional protein-purification method such as salting-out, gel filtration, ion exchange chromatography, adsorption chromatography, affinity chromatography, ultrafiltration or preparative reversed phase HPLC, to obtain the objective modified peptides.

The modified peptides of the present invention can be formulated into suitable pharmaceutical preparations such as capsules and injections in admixture with carriers, diluents, etc. known per se, which can be orally or parenterally administered to mammals (e.g. cows, horses, pigs, sheep, humans).

For example, in the case where the chemically modified SOD as obtained in accordance with Example 2 is administered for the treatment of acute myocardial infarction, the daily dose is usually 1-100 mg, which is administered in one dose or several times in divided doses.

The polyethylene glycol derivatives (I) of the present invention are capable of modifying amino groups in peptides.

In addition, the polyethylene glycol derivatives (I) of the present invention have a characteristic feature in that the modification reaction can be conducted in a wider range of pH.

The peptides modified by the polyethylene glycol derivatives (I), as compared with the corresponding non-modified peptides, are decreased in antigenicity, are considerably delayed in biological clearance (i.e. the durability is extended) and exhibit their physiological activities effectively over a long period. Besides, the modified peptides retain the physiological activities which the non-modified peptides possess. Thus, the modified peptides are very effective as pharmaceuticals as well as drugs for animals.

The present invention is explained in further detail by the following examples, which are not limitative to the present invention.

In the following description, each abbreviation means the following, respectively.

| | |
|---|---|
| Asx: aspartic acid or asparagine | |
| Glx.: glutamic acid or glutamine | |
| Ser.: serine, | Gly.: glycine |
| His.: histidine, | Arg.: arginine |
| Thr.: threonine, | Ala.: alanine |
| Pro.: proline, | Tyr.: tyrosine |
| Val.: valine, | Met.: methionine |
| Ile.: isoleusine, | Leu.: leusine |
| Phe.: phenylalanine, | Lys.: lysine |

EXAMPLE 1

Production of 3,5-bis-methoxypolyethylene glycol benzoic acid and its N-hydroxysuccinimide ester (1) Production of monomethoxypolyethylene glycol tosylate

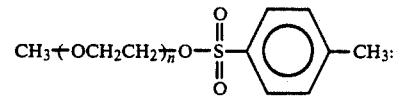

Polyethylene glycol monomethyl ether (average molecular weight 4500, 100 g) was dissolved in a mixed solvent of 400 ml of toluene and 200 ml of methylene chloride.

Triethylamine (20 ml) was added thereto, followed by addition of p-toluenesulfonyl chloride (36 g). The mixture was stirred at room temperature for 5 hours. Thereafter, triethylamine (20 ml) and p-toluenesulfonyl chloride (30 g) was further added, and the mixture was stirred for 10 hours. The insoluble matters were filtered off, and the filtrate was evaporated to dryness under reduced pressure. The residue obtained was purified by silica gel column chromatography to give 100.5 g of the title monomethoxypolyethylene glycol tosylate (Yield 97.2%).

Reversed phase high performance liquid chromatography

Column: YMC-ODS, 5μ, φ4.6×250 mm
Eluent: Gradient
  A Solution: Water (containing 0.1% trifluoroacetic acid)
  B Solution: Acetonitrile (containing 0.1% trifuluoroacetic acid)
  Initial concentration of B Solution: 30%
  Concentration gradient: 1%/min.
Flow rate: 1 ml/min., Detection wavelength: 214 nm
Retention time: 21.8 minutes (2) Production of 3,5-bis-methoxypolyethylene glycol benzoic acid

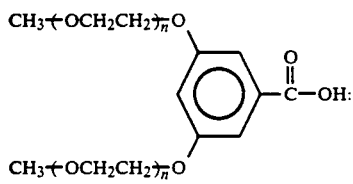

Monomethoxypolyethylene glycol tosylate (4.00 g) as obtained in (1) and 3,5-dihydroxybenzoic acid (34 mg) were dissolved in N,N-dimethylformamide (30 ml). Potassium carbonate (1.665 g) was added thereto, and the mixture was stirred in an oil bath at 110° C. for 2 hours. The insoluble matters were filtered off, and the filtrate was evaporated to dryness under reduced pressure. The residue was dissolved in water (50 ml), added with 1N sodium hydroxide (50 ml) and stirred at 50° C. for 1 hour. The mixture was neutralized with 1N hydrochloric acid and pH was adjusted to 4.0 with 50% acetic acid. Thereafter, the mixture was subjected to ultrafiltration (Millipore Corp. Pellicon cassette system, membrane PT-10,000) to purify and desalt, after which concentration was conducted by ultrafiltration (Amicon Corp. membrane YM-10) to give the desired aqueous solution. The solvent was distilled off under reduced pressure to give 1.19 g of the title 3,5-bis-methoxypolyethylene glycol benzoic acid.

Reversed phase high performance liquid chromatography

Column: YMC-ODS, 5μ, φ4.6×250 mm
Eluent: Gradient
  A Solution: Water (containing 0.1% trifluoroacetic acid)
  B Solution: Acetonitrile (containing 0.1% trifuluoroacetic acid)
  Initial concentration of B Solution: 30%
  Concentration gradient: 1%/min.
Flow rate: 1 ml/min., Detection wavelength: 214 nm
Retention time: 18.22 minutes High performance gel filtration chromatography
Column: TSK gel G3000 PW, φ7.5×600 mm (Manufactured by Toso Corp.)
Eluent: 0.2M NaCl
Flow rate: 0.6 ml/min., Detection wavelength: 220 nm
Retention time: 22.09 minutes High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 26.81 minutes (3) Production of 3,5-bis-methoxypolyethylene glycol benzoic acid N-hydroxysuccinimide ester

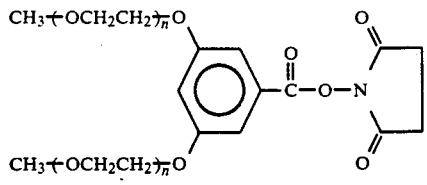

3,5-bis-Methoxypolyethylene glycol benzoic acid (1.182 g) as obtained in (2) was dissolved in N,N-dimethylformamide (10 ml), and thereto were added N-hydroxysuccinimide (180 mg) and 0.5M dicyclohexylcarbodiimide in methylene chloride (3.11 ml), followed by stirring at room temperature for 27 hours. The resultant precipitate was filtered off, and diethyl ether (200 ml) was dropwise added to the filtrate, followed by filtration of the newly resulted precipitate. The precipitate was washed with diethyl ether, and dried at room temperature for 12 hours to give 1.163 g of the title 3,5-bis-methoxypolyethylene glycol benzoic acid N-hydroxysuccinimide ester (Yield 97%).

Reversed phase high performance liquid chromatography

Column: YMC-ODS, 5μ, φ4.6×250 mm
Eluent: Gradient
  A Solution: Water (containing 0.1% trifluoroacetic acid)
  B Solution: Acetonitrile (containing 0.1% trifuluoroacetic acid)
  Initial concentration of B Solution: 30%
  Concentration gradient: 1%/min.
Flow rate: 1 ml/min., Detection wavelength: 214 nm
Retention time: 18.76 minutes High performance gel filtration chromatography
Column: TSK gel G3000 PW, φ7.5×600 mm (Manufactured by Toso Corp.)
Eluent: 0.2M NaCl
Flow rate: 0.6 ml/min., Detection wavelength: 220 nm
Retention time: 22.97 minutes High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 26.81 minutes

EXAMPLE 2

Production of superoxide dismutase modified by a polyethylene glycol derivative (I) (PEG-modified SOD)

To 5.0 mg of Cu, Zn-SOD derived from human in 2.5 ml of a 0.1M borate buffer (pH 8.21) was added 189 mg of 3,5-bis-methoxypolyethylene glycol benzoic acid N-hydroxysuccinimide ester as obtained in Example 1 (6 equivalent amount relative to the amino group) and the mixture was stirred at room temperature for 3 hours. After adjusting the pH to 5.5 with 20% AcOH, it was purified by gel filtration on Sephacryl S-200 column (Pharmacia Corp., φ2.6×81 cm). Thereafter, the objective fraction was subjected to desalting and concentration by ultrafiltration with the use of YM-30 membrane manufactured by Amicon Corp., USA, and thereby 1.8 ml of the solution containing the objective compound was obtained (contained protein: 1.283 mg/ml).

The results of the amino acid analysis by 24 hours' treatment for acid decomposition of the objective compound with 6N hydrochloric acid-phenol at 110° C.:

Asx. 31.8 (36); Glx. 23.7 (26); Ser. 17.2 (20); Gly. 43.9 (50); His. 14.4 (16); Arg. 7.16 (8); Thr. 14.7 (16); Ala. *20.0 (20); Pro. 9.63 (10); Val. 21.6 (28); Ile. 11.0 (18); Leu. 16.5 (18); Phe. 6.70 (8); Lys. 15.7 (22)

(* means standard amino acid and the figures in parentheses are theoretical values)

Reversed phase high performance liquid chromatography

Column: YMC-ODS, 5μ, φ4.6×250 mm
Eluent: Gradient
  A Solution: Water (containing 0.1% trifluoroacetic acid)
  B Solution: Acetonitrile (containing 0.1% trifuluoroacetic acid)
  Initial concentration of B Solution: 30%
  Concentration gradient: 1%/min.
Flow rate: 1 ml/min., Detection wavelength: 214 nm
Retention time: 18.9 minutes High performance gel filtration chromatography
Column: TSK gel G3000 PW, φ7.5×600 mm (Manufactured by Toso Corp.)
Eluent: 0.2M NaCl
Flow rate: 0.6 ml/min., Detection wavelength: 220 nm
Retention time: 20.05 minutes High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 17.37 minutes

EXAMPLE 3

Production of insulin-like growth factor-I modified by a polyethylene glycol derivative (I) (PEG-modified IGF-I)

To 1.09 mg of IGF-I in 500 μl of a 0.1M borate buffer (pH 8.21) was added 10.9 mg of 3,5-bis-methoxypolyethylene glycol benzoic acid N-hydroxysuccinimide ester as obtained in Example 1 (2 equivalent amount relative to the amino group), and the mixture was stirred at room temperature for 5.5 hours. After adjusting the pH to 4.74 with 10% acetic acid, the mixture was purified by gel filtration on Sephacryl S-200 column (Pharmacia Corp., φ2.6×81 cm), and the objective fraction was subjected to desalting and concentration by ultrafiltration with the use of YM-10 membrane manufactured by Amicon Corp. to give 1.8 ml of an aqueous solution containing the objective compound (contained protein: 359 μg/ml).

The results of the amino acid analysis by 24 hours' treatment for acid decomposition of the objective compound with 6N hydrochloric acid-phenol at 110° C.:

Asx. 4.89 (5); Glx. 5.44 (6); Ser. 4.68 (5); Gly. 7.05 (7); Arg. 6.00 (6); Thr. 2.85 (3); Ala. 6.14 (6); Pro. 4.87 (5); Tyr. 2.91 (3); Val. 2.41 (3); Met. 0.70 (1); Ile. 0.72 (1); Leu. *6.00 (6); Phe. 3.92 (4); Lys. 2.70 (3)

(* means standard amino acid and the figures in parentheses are theoretical values)

Reversed phase high performance liquid chromatography

Column: YMC-ODS, 5μ, φ4.6×250 mm
Eluent: Gradient
  A Solution: Water (containing 0.1% trifluoroacetic acid)
  B Solution: Acetonitrile (containing 0.1% trifuluoroacetic acid)
  Initial concentration of B Solution: 25%
  Concentration gradient: 1%/min.
Flow rate: 1 ml/min., Detection wavelength: 214 nm
Retention time: 23.5 minutes High performance gel filtration chromatography
Column: TSK gel G3000 PW, φ7.5×600 mm (Manufactured by Toso Corp.)
Eluent: 0.2M NaCl
Flow rate: 0.6 ml/min., Detection wavelength: 220 nm
Retention time: 20.68 minutes

EXAMPLE 4

Production of insulin-like growth factor-II modified by a polyethylene glycol derivative (I) (PEG-modified IGF-II)

To 1.0 mg of IGF-II in 1 ml of a 0.1M borate buffer (pH 8.21) was added 8 mg of 3,5-bis-methoxypolyethylene glycol benzoic acid N-hydroxysuccinimide ester as obtained in Example 1, and the mixture was stirred at room temperature for 1.5 hours. The modifying reagent (10 mg) was further added (6.75 equivalent amount in total relative to the amino group), followed by 13 hours' stirring. After adjusting the pH to 5.5 with 10% AcOH, the reaction mixture was purified by gel filtration on Sephacryl S-200 column (Pharmacia Corp., φ2.6×81 cm), and the objective 2 fractions ①, ② were subjected to desalting and concentration by ultrafiltration with the use of YM-10 membrane manufactured by Amicon Corp. to give 1 ml each of an aqueous solution containing the objective compound (contained protein in ①: 59.1 μg/ml, contained protein in ②: 29.4 μg/ml).

The results of the amino acid analysis by 24 hours' treatment for acid decomposition of the objective compound with 6N hydrochloric acid-phenol at 110° C.:

①: Asx. 2.92 (3); Glx. 6.21 (7); Ser. 6.17 (7); Gly. 4.60 (5); Arg. 6.49 (8); Thr. 3.71 (4); Ala. *5.00 (5); Pro. 2.79 (3); Tyr. 2.27 (3); Val. 2.90 (4); Met. 0.18 (1); Ile. 0.72 (1); Leu. 5.52 (6); Phe. 2.72 (4); Lys. 1.03 (1)

(* means standard amino acid and the figures in parentheses are theoretical values)

②: Asx. 2.84 (3); Glx. 6.37 (7); Ser. 6.30 (7); Gly. 4.38 (5); Arg. 7.00 (8); Thr. 3.51 (4); Ala. 5.04 (5); Pro. 2.73 (3); Tyr. 2.15 (3); Val. 3.01 (4); Met. 0.18 (1); Ile. 2.02 (1); Leu. *6.00 (6); Phe. 2.80 (4); Lys. 0.83 (1)

(* means standard amino acid and the figures in parentheses are theoretical values)

High performance gel filtration chromatography
Column: TSK gel G3000 PW, φ7.5×600 mm (Manufactured by Toso Corp.)
Eluent: 0.2M NaCl
Flow rate: 0.6 ml/min., Detection wavelength: 220 nm
Retention time ①: 20.68 minutes
Retention time ②: 21.24 minutes High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time ①: 21.74 minutes
Retention time ②: 23.41 minutes

EXAMPLE 5

Production of calcitonin gene related peptide modified by a polyethylene glycol derivative (I) (PEG-modified CGRP)

To 1.00 mg of CGRP in 500 μl of a 0.1M borate buffer (pH 8.21) was added 22 mg of 3,5-bis-methoxypolyethylene glycol benzoic acid N-hydroxysuccinimide ester as obtained in Example 1 (3 equivalent amount relative to the amino group), and the mixture was stirred at room temperature for 4 hours. After adjusting the pH to 6.0 with 10% AcOH, the reaction mixture was purified by gel filtration on Sephacryl S-200 column (Pharmacia Corp., φ2.6×81 cm), and the objective 2 fractions ①, ② were subjected to desalting and concentration by ultra-filtration with the use of YM-10 membrane manufactured by Amicon Corp. to give 1 ml each of an aqueous solution containing the objective compound (contained protein in ①: 74.2 μg/ml, contained protein in ②: 112 μg/ml).

The results of the amino acid analysis by 24 hours' treatment for acid decomposition of the objective compound with 6N hydrochloric acid-phenol at 110° C.:

①: Asx. 3.70 (4); Ser. 3.18 (3); Gly. 4.58 (4); His. 0.98 (1); Arg. 1.94 (2); Thr. 3.80 (4); Ala. *4.00 (4); Pro. 1.06 (1); Val. 3.89 (5); Leu. 3.04 (3); Phe. 1.93 (2); Lys. 1.92 (2)

(* means standard amino acid and the figures in parentheses are theoretical values)

②: Asx. 4.28 (4); Ser. 3.33 (3); Gly. 4.51 (4); His. 1.02 (1); Arg. 2.06 (2); Thr. 3.99 (4); Ala. 3.92 (4); Pro. 1.11 (1); Val. 4.52 (5); Leu. *3.00 (3); Phe. 2.08 (2); Lys. 2.21 (2)

(* means standard amino acid and the figures in parentheses are theoretical values)

High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time ①: 20.78 minutes
Retention time ②: 22.32 minutes

EXAMPLE 6

Production of elastase modified by a polyethylene glycol derivative (I) (PEG-modified elastase)

To 1.00 mg of swine elastase in 500 μl of a 0.1M borate buffer (pH 8.21) was added 7.1 mg of 3,5-bis-methoxypolyethylene glycol benzoic acid N-hydroxysuccinimide ester obtained in Example 1 (5 equivalent amount relative to the amino group), and the mixture was stirred at room temperature for 24 hours. After adjusting the pH to 6.0 with 10% AcOH, the reaction mixture was purified by gel filtration on Sephacryl S-200 column (Pharmacia Corp., φ2.6×81 cm), and the objective fraction was subjected to desalting and concentration by ultrafiltration with the use of YM-10 membrane manufactured by Amicon Corp. to give 1 ml of an aqueous solution containing the objective compound (contained protein: 64 μg/ml).

The results of the amino acid analysis by 24 hours' treatment for acid decomposition of the objective compound with 6N hydrochloric acid-phenol at 110° C.:

Asx. 22.2 (24); Glx. 19.1 (19); Ser. 20.8 (22); Gly. 25.5 (25); His. 5.75 (6); Arg. 11.3 (12); Thr. 18.2 (19); Ala. *17.0 (17); Pro. 7.37 (7); Tyr. 10.1 (11); Val. 21.5 (27); Met. 0.77 (2); Ile. 9.88 (10); Leu. 17.1 (18); Phe. 2.99 (3); Lys. 3.59 (3)

(* means standard amino acid and the figures in parentheses are theoretical values)

High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 22.62 minutes

EXAMPLE 7

Production of 3,4-bis-methoxypolyethylene glycol dihydrocinnamic acid and its N-hydroxysuccinimide ester (1) Production of monomethoxypolyethylene glycol tosylate

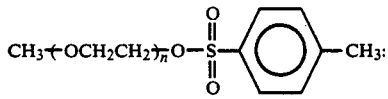

Polyethylene glycol monomethyl ether (average molecular weight 5,000, 100 g) was dissolved in a mixed solvent of 250 ml of methylene chloride and 500 ml of toluene. Triethylamine (15 ml) and p-toluenesulfonyl chloride (20 g) were added thereto, and the mixture was stirred at room temperature for 7 hours. Thereafter, triethylamine (15 ml) and p-toluenesulfonyl chloride (20 g) were further added, and the mixture was stirred for 17 hours. The insoluble matters were filtered off, and the filtrate was evaporated to dryness under reduced pressure. The residue obtained was purified by silica gel column chromatography to give 98 g of the title monomethoxypolyethylene glycol tosylate.

Reversed phase high performance liquid chromatography
Column: YMC-ODS, 5μ, φ4.6×250 mm
Eluent: Gradient
  A Solution: Water (containing 0.1% trifluoroacetic acid)
  B Solution: Acetonitrile (containing 0.1% trifluoroacetic acid)
  Initial concentration of B Solution: 30%
  Concentration gradient: 1%/min.
Flow rate: 1 ml/min., Detection wavelength: 220 nm
Retention time: 20.33 minutes High performance gel filtration chromatography
Column: TSK gel G3000 PW, φ7.5 ×600 mm (Manufactured by Toso Corp.)
Eluent: 0.2M NaCl
Flow rate: 0.6 ml/min., Detection wavelength: 220 nm
Retention time: 25.61 minutes (2) Production of 3,4-dihydroxydihydrocinnamic acid methyl ester

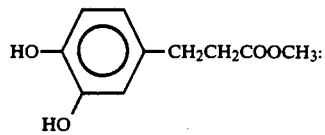

3,4-Dihydroxydihydrocinnamic acid (5 g) was dissolved in N,N-dimethylformamide (20 ml), and 4-N,N-dimethylaminopyridine (305 mg) and methyl alcohol (15 ml) were added thereto, followed by cooling to 5° C. Thereto was added 1-ethyl-3-(3-dimethylaminopropyl)carbodiimide (5.72 g), and the mixture was stirred at 5° C. for 30 minutes and at room temperature for 4 hours. Ethyl acetate was added to the reaction mixture, and it was washed with a 5% aqueous solution of citric acid, a saturated aqueous solution of sodium bicarbonate and a saturated aqueous solution of sodium chloride and dried over MgSO4. The desiccating agent was filtered off, and the filtrate was evaporated to dryness under reduced pressure to give 5 g of a crude product which was then purified by silica gel column chromatography to give 2.237 g of the title compound.

Thin-layer chromatography
Kiesel gel 60F$_{254}$, CHCl$_3$:MeOH=10:1 Rf=0.5

(3) Production of 3,4-bis-methoxypolyethylene glycol dihydrocinnamic acid

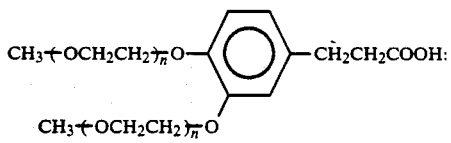

Monomethoxypolyethylene glycol tosylate (41.3 g) as obtained in (1) and 3,4-dihydroxydihydrocinnamic acid methyl ester (400 mg) as obtained in (2) were dissolved in 100 ml of N,N-dimethylformamide. Potassium carbonate (5.244 g) was added thereto, and the mixture was stirred in an oil bath at 110° C. for 7 hours. The insoluble matters were filtered off, and the filtrate was evaporated to dryness under reduced pressure. 1N Sodium hydroxide (300 ml) was added to the residue and the mixture was stirred under heating at 50° C. for 1 hour. After cooling, the mixture was neutralized with 1N HCl, purified by ultrafiltration (Pellicon cassette system by Millipore Corp., membrane: PT-10,000) and evaporated to dryness under reduced pressure. Thereafter, it was purified by silica gel column chromatography to give 3.8 g of the title 3,4-bis-methoxypolyethylene glycol dihydrocinnamic acid.

Reversed phase high performance liquid chromatography
Column: YMC-ODS, 5μ, φ4.6×250 mm
Eluent: Gradient
  A Solution: Water (containing 0.1% trifluoroacetic acid)
  B Solution: Acetonitrile (containing 0.1% trifluoroacetic acid)
  Initial concentration of B Solution: 30%
  Concentration gradient: 1%/min.
Flow rate: 1 ml/min., Detection wavelength: 220 nm
Retention time: 19.08 minutes
High performance gel filtration chromatography
Column: TSK gel G3000 PW, φ7.5×600 mm (Manufactured by Toso Corp.)
Eluent: 0.2M NaCl
Flow rate: 0.6 ml/min.
Detection: UV 220 nm, differential refraction
Retention time: 22.1 minutes
High performance gel filtration chromatography
Column: TSK gel G4000 PW$_{XL}$×2, (φ7.8×300 mm)×2 (Manufactured by Toso Corp.)
Eluent: 0.2M NaCl
Flow rate: 0.6 ml/min.
Detection: UV 220 nm, differential refraction
Retention time: 28.04 minutes (4) Production of 3,4-bis-methoxypolyethylene glycol dihydrocinnamic acid N-hydroxysuccinimide ester

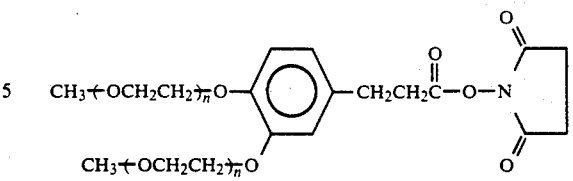

To 3,4-bis-methoxypolyethylene glycol dihydrocinnamic acid (1.5 g) as obtained in (3) in N,N-dimethylformamide (15 ml) were added N-hydroxysuccinimide (172.7 mg) and 0.5M dicyclohexylcarbodiimide in a methylene chloride solution (3 ml), and the mixture was stirred at room temperature for 24 hours. The precipitate was filtered off, diethyl ether (300 ml) was dropwise added to the filtrate, and newly resulted precipitate was filtered off. The precipitate was washed with diethyl ether, dried at room temperature for 12 hours to give 1.4 g of the title 3,4-bis-methoxypolyethylene glycol dihydrocinnamic acid N-hydroxysuccinimide ester.

Reversed phase high performance liquid chromatography
Column: YMC-ODS, 5μ, φ4.6×250 mm
Eluent: Gradient
  A Solution: Water (containing 0.1% trifluoroacetic acid)
  B Solution: Acetonitrile (containing 0.1% trifluoroacetic acid)
  Initial concentration of B Solution: 30%
  Concentration gradient: 1%/min.
Flow rate: 1 ml/min., Detection wavelength: 214 nm
Retention time: 21.30 minutes
High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 25.71 minutes

EXAMPLE 8

Production of superoxide dismutase modified by a polyethylene glycol derivative (I) (PEG-modified SOD)

To 5.0 mg of Cu, Zn-SOD derived from human in 2.5 ml of a 0.1M borate buffer (pH 8.21) was added 3,4-bis-methoxypolyethylene glycol dihydrocinnamic acid N-hydroxysuccinimide ester (35 mg, 1 equivalent amount relative to the amino group) as obtained in Example 7, and the mixture was stirred at room temperature for 1 hour. Then, the reaction mixture was purified by gel filtration on Sephacryl S-200 (Pharmacia Corp., φ2.6×81 cm). Thereafter, the objective fraction was subjected to desalting and concentration by ultrafiltration with the use of YM-30 membrane manufactured by Amicon Corp., thereby 1.8 ml of the solution containing the objective compound was obtained (contained protein: 900 μg/ml).

The results of the amino acid analysis by 24 hours' treatment for acid decomposition of the objective compound with 6N hydrochloric acid-phenol at 110° C.
  Asx. 32.4 (36); Glx. 24.9 (26); Ser. 17.8 (20); Gly. 49.6 (50); His. 15.9 (16); Arg. 7.29 (8); Thr. 14.9 (16); Ala. 20.1 (20); Pro. 9.91 (10); Val. 24.9 (28); Ile. 14.0 (18); Leu. *18.0 (18); Phe. 7.58 (8); Lys. 20.9 (22)
(* means standard amino acid and the figures in parentheses are theoretical values)

High performance gel filtration chromatography
Column: TSK gel G3000 SW, $\phi 7.5 \times 600$ mm (Manufactured by Toso Corp.)
Eluent: 0.2M NaCl (containing 5% EtOH)
Flow rate: 0.6 ml/min., Detection wavelength: 220 nm
Retention time: 20.03 minutes

EXAMPLE 9

Production of superoxide dismutase modified by a polyethylene glycol derivative (I) (PEG-modified SOD)

To 5.0 mg of Cu,Zn-SOD derived from human in 2.5 ml of a 0.1M borate buffer (pH 8.21) was added 3,4-bis-methoxypolyethylene glycol dihydrocinnamic acid N-hydroxysuccinimide ester (175 mg, 5 equivalent amount relative to the amino group) as obtained in Example 7, and the mixture was stirred at room temperature for 1 hour. Then, the reaction mixture was purified by gel filtration on Sephacryl S-200 (Pharmacia Corp., $\phi 2.6 \times 81$ cm). Thereafter, the objective fraction was subjected to desalting and concentration by ultrafiltration with the use of YM-30 membrane manufactured by Amicon Corp., thereby 1.8 ml of the solution containing the objective compound was obtained (contained protein: 1.59 mg/ml).

The results of the amino acid analysis by 24 hours' treatment for acid decomposition of the objective compound with 6N hydrochloric acid-phenol at 110° C.:

Asx. 32.6 (36); Glx. 24.8 (26); Ser. 17.8 (20); Gly. 50.5 (50); His. 16.3 (16); Arg. 7.35 (8); Thr. 15.3 (16); Ala. 20.8 (20); Pro. 10.1 (10); Val. 25.3 (28); Ile. 14.2 (18); Leu. *18.0 (18); Phe. 7.95 (8); Lys. 20.5 (22)

(* means standard amino acid and the figures in parentheses are theoretical values)

High performance gel filtration chromatography
Column: TSK gel G3000 SW, $\phi 7.5 \times 600$ mm (Manufactured by Toso Corp.)
Eluent: 0.2M NaCl (containing 5% EtOH)
Flow rate: 0.6 ml/min., Detection wavelength: 220 nm
Retention time: 18.45 minutes

EXAMPLE 10

Production of insulin-like growth factor-I modified by a polyethylene glycol derivative (I) (PEG-modified IGF-I)

To 3.0 mg of IGF-I in 1.5 ml of a 0.1M borate buffer (pH 8.21) was added 3,4-bis-methoxypolyethylene glycol dihydrocinnamic acid N-hydroxysuccinimide ester (49 mg, 3 equivalent amount relative to the amino group) as obtained in Example 7, and the mixture was stirred at room temperature for 1 hour. The modifying reagent (49 mg) was further added thereto, and the mixture was stirred for 1 hour, followed by purification by gel filtration on Sephacryl S-200 (Pharmacia Corp., $\phi 2.6 \times 81$ cm). Thereafter, the objective fraction was subjected to desalting and concentration by ultrafiltration with the use of YM-10 membrane manufactured by Amicon Corp., thereby 1.8 ml of the solution containing the objective compound was obtained (contained protein: 200 μg/ml).

The results of the amino acid analysis by 24 hours' treatment for acid decomposition of the objective compound with 6N hydrochloric acid-phenol at 110° C.:

Asx. 4.56 (5); Glx. 5.30 (6); Ser. 4.44 (5); Gly. 7.25 (7); Arg. 6.54 (6); Thr. 2.80 (3); Ala. *6.00 (6); Pro. 4.78 (5); Tyr. 2.93 (3); Val. 2.46 (3); Met. 1.44 (1); Ile. 0.72 (1); Leu. 5.93 (6); Phe. 4.00 (4); Lys. 2.89 (3)

(* means standard amino acid and the figures in parentheses are theoretical values)

High performance gel filtration chromatography
Column: TSK gel G3000 SW, $\phi 7.5 \times 600$ mm (Manufactured by Toso Corp.)
Eluent: 0.2M NaCl (containing 5% EtOH)
Flow rate: 0.6 ml/min., Detection wavelength: 220 nm
Retention time: 22.08 minutes

EXAMPLE 11

Production of calcitonin gene related peptide modified by a polyethylene glycol derivative (I) (PEG-modified CGRP)

To 3.0 mg of CGRP in 1.5 ml of a 0.1M borate buffer (pH 8.21) was added 3,4-bis-methoxypolyethylene glycol dihydrocinnamic acid N-hydroxysuccinimide ester (119 mg, 5 equivalent amount relative to the amino group) as obtained in Example 7, and the mixture was stirred at room temperature for 2 hours. Then, the reaction mixture was purified by gel filtration on Sephacryl S-200 (Pharmacia Corp., $\phi 2.6 \times 81$ cm). Thereafter, the objective fraction was subjected to desalting and concentration by ultrafiltration with the use of YM-10 membrane manufactured by Amicon Corp., thereby 1.8 ml of the solution containing the objective compound was obtained (contained protein: 154 μg/ml).

The results of the amino acid analysis by 24 hours' treatment for acid decomposition of the objective compound with 6N hydrochloric acid-phenol at 110° C.:

Asx. 3.74 (4); Ser. 2.68 (3); Gly. 4.29 (4); His. 0.83 (1); Arg. 2.03 (2); Thr. 3.48 (4); Ala. 3.86 (4); Pro. 1.01 (1); Val. 4.12 (5); Leu. *3.00 (3); Phe. 2.08 (2); Lys. 1.70 (2);

(* means standard amino acid and the figures in parentheses are theoretical values)

High performance gel filtration chromatography
Column: TSK gel G3000 SW, $\phi 7.5 \times 600$ mm (Manufactured by Toso Corp.)
Eluent: 0.2M NaCl (containing 5% EtOH)
Flow rate: 0.6 ml/min., Detection wavelength: 220 nm
Retention time: 16.42 minutes

EXAMPLE 12

Production of elastase modified by a polyethylene glycol derivative (I) (PEG-modified elastase)

To 3.0 mg of swine elastase in 2.5 ml of a 0.1M borate buffer (pH 8.21) was added 3,4-bis-methoxypolyethylene glycol dihydrocinnamic acid N-hydroxysuccinimide ester (111 mg, 20 equivalent amount relative to the amino group) as obtained in Example 7, and the mixture was stirred for 5 hours. Then, the reaction mixture was purified by gel filtration on Sephacryl S-200 (Pharmacia Corp., $\phi 2.6 \times 81$ cm). Thereafter, the objective fraction was subjected to desalting and concentration by ultrafiltration with the use of YM-10 membrane manufactured by Amicon Corp., thereby 1 ml of the solution containing the objective compound was obtained (contained protein: 90 μg/ml).

The results of the amino acid analysis by 24 hours' treatment for acid decomposition of the objective compound with 6N hydrochloric acid-phenol at 110° C.:

Asx. 20.4 (24); Glx. 15.5 (19); Ser. 17.4 (22); Gly. 29.2 (25); His. 4.23 (6); Arg. 11.6 (12); Thr. 14.4 (19); Ala. 17.4 (17); Pro. 7.31 (7); Tyr. 6.67 (11); Val. 16.3 (27); Met. 2.37 (2); Ile. 8.39 (10); Leu. *18.0 (18); Phe. 6.81 (3); Lys. 6.88 (3);

(* means standard amino acid and the figures in parentheses are theoretical values)

High performance gel filtration chromatography
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 16.54 minutes

EXAMPLE 13

Production of growth hormone-releasing factor modified by a polyethylene glycol derivative (I) [PEG-modified GRF (1-44)NH₂]

To 3.0 mg of GRF(1-44)NH₂ in 1.5 ml of a 0.1M borate buffer (pH 8.21) was added 3,4-bis-methoxypolyethylene glycol dihydrocinnamic acid N-hydroxysuccinimide ester (120 mg, 5 equivalent amount relative to the amino group) as obtained in Example 7, and the mixture was stirred at room temperature for 1 hour. Then, the reaction mixture was purified by gel filtration on Sephacryl S-200 (Pharmacia Corp., φ2.6×81 cm). Thereafter, the objective fraction was subjected to desalting and concentration by ultrafiltration with the use of YM-10 membrane manufactured by Amicon Corp., thereby 1.8 ml of the solution containing the objective compound was obtained (contained protein: 86 μg/ml).

The results of the amino acid analysis by 24 hours' treatment for acid decomposition of the objective compound with 6N hydrochloric acid-phenol at 110° C.:

Asx. 3.48 (4); Glx. 6.21 (7); Ser. 3.42 (4); Gly. 3.13 (3); Arg. 6.07 (6); Thr. 0.94 (1); Ala. 4.75 (5); Tyr. 1.73 (2); Val. 0.93 (1); Met. 0.42 (1); Ile. 2.01 (2); Leu. *5.00 (5); Phe. 0.98 (1); Lys. 1.65 (2)

(* means standard amino acid and the figures in parentheses are theoretical values)

High performance gel filtration chromatogrphy
Column: TSK gel G3000 SW, φ7.5×600 mm (Manufactured by Toso Corp.)
Eluent: 0.2M NaCl (containing 5% EtOH)
Flow rate: 0.6 ml/min., Detection wavelength: 220 nm
Retention time: 22.08 minutes

What is claimed is:

1. A polyethylene glycol derivative of the formula

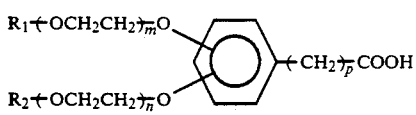
(I)

wherein $R_1$ and $R_2$ are the same or different and each represents a lower alkyl, m and n are the same or different and each represents a positive integer of 10 to 400, and p is 0 or a positive integer.

2. A polyethylene glycol derivative as claimed in claim 1 wherein p is 0 or a positive integer of 1 to 10.

3. A polyethylene glycol derivative as claimed in claim 1 which is selected from the group consisting of 3,5-bis-methoxypolyethylene glycol dihydrocinnamic acid.

4. A modified peptide wherein amino groups in the peptide are modified by a polyethylene glycol derivative as claimed in claim 1.

5. A modified peptide as claimed in claim 4 wherein the peptide has 2 or more amino acids bound by peptide bonds and at least one of the constituent amino acids has a free amino group.

6. A modified peptide as claimed in claim 4 wherein the peptide is selected from the group consisting of superoxide dismutase, insulin-like growth factor-I, insulin-like growth factor-II, calcitonin gene related peptide, elastase and growth hormone-releasing factor.

7. A modified peptide as claimed in claim 4 which is selected from the group consisting of superoxide dismutase modified by 3,5-bis-methoxypolyethylene glycol benzoic acid, insulin-like growth factor-I modified by 3,5-bis-methoxypolyethylene glycol benzoic acid, insulin-like growth factor-II modified by 3,5-bis-methoxypolyethylene glycol benzoic acid, calcitonin gene related peptide modified by 3,5-bis-methoxypolyethylene glycol benzoic acid, elastase modified by 3,5-bis-methoxypolyethylene glycol benzoic acid, superoxide dismutase modified by 3,4-bis-methoxypolyethylene glycol dihydrocinnamic acid, insulin-like growth factor-I modified by 3,4-bis-methoxypolyethylene glycol dihydrocinnamic acid, calcitonin gene related peptide modified by 3,4-bis-methoxypolyethylene glycol dihydrocinnamic acid, elastase modified by 3,4-bis-methoxypolyethylene glycol dihydrocinnamic acid and growth hormone-releasing factor modified by 3,4-bis-methoxypolyethylene glycol dihydrocinnamic acid.

8. A method for producing a polyethylene glycol derivative as claimed in claim 1 comprising reacting a compound of the formula (III) of (III')

(III)

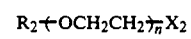
(III')

wherein $X_1$ and $X_2$ are the same or different and each represents an alkylsulfonyloxy, an aromatic sulfonyloxy or a halogen, and $R_1$, $R_2$, m and n are as defined in claim 1, with a compound of the formula (IV)

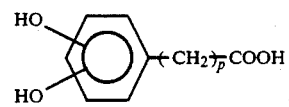
(IV)

wherein p is as defined in claim 1.

9. A pharmaceutical composition comprising a modified peptide as claimed in claim 4 and a pharmaceutically acceptable carrier.

10. A pharmaceutical composition comprising a modified peptide as claimed in claim 5 and a pharmaceutically acceptable carrier.

11. A pharmaceutical composition comprising a modified peptide as claimed in claim 6 and a pharmaceutically acceptable carrier.

12. A pharmaceutical composition comprising a modified peptide as claimed in claim 7 and a pharmaceutically acceptable carrier.

13. A method for producing a modified peptide comprising reacting a carboxyl group-activated compound of a polyethylene glycol derivative of the formula

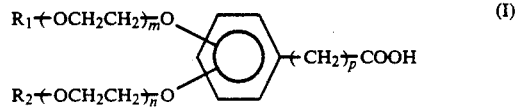
(I)

wherein $R_1$ and $R_2$ are the same or different and each represents a lower alkyl, m and n are the same or different and each represents a positive integer and p is 0 or a positive integer, with a peptide having at least one free amino group.

14. A method as claimed in claim 13 wherein m and n are respectively a positive integer of 10 to 400.

* * * * *